United States Patent
Mogensen et al.

(10) Patent No.: US 7,594,909 B2
(45) Date of Patent: Sep. 29, 2009

(54) APPARATUS AND METHOD FOR ADJUSTMENT OF THE LENGTH OF AN INFUSION TUBING

(75) Inventors: Lasse Wesseltoft Mogensen, Søborg (DK); Magnus Walter Göransson, Göteborg (SE)

(73) Assignee: Unomedical, A/S, Birkeroed (DK)

( * ) Notice: Subject to any disclaimer, the term of this patent is extended or adjusted under 35 U.S.C. 154(b) by 833 days.

(21) Appl. No.: 10/517,194

(22) PCT Filed: Sep. 2, 2003

(86) PCT No.: PCT/DK03/00572

§ 371 (c)(1),
(2), (4) Date: Dec. 6, 2004

(87) PCT Pub. No.: WO2004/020023

PCT Pub. Date: Mar. 11, 2004

(65) Prior Publication Data
US 2005/0234423 A1 Oct. 20, 2005

(30) Foreign Application Priority Data
Sep. 2, 2002 (DK) ............................... 2002 01286

(51) Int. Cl.
*A61M 31/00* (2006.01)
*A61M 5/32* (2006.01)
(52) U.S. Cl. ...................... 604/500; 604/174
(58) Field of Classification Search ............ 242/378.4, 242/378, 378.1, 388.6, 388.7, 388.1; 604/500, 604/174, 177, 180
See application file for complete search history.

(56) References Cited

U.S. PATENT DOCUMENTS

| 643,544 A | 2/1900 | Simmons |
|---|---|---|
| 1,838,825 A | 12/1931 | Goldstein |
| 1,991,103 A | 2/1935 | King |
| 2,047,010 A | 7/1936 | Dickinson |
| 2,295,849 A | 9/1942 | Kayden |
| 2,319,731 A | 5/1943 | Garrett |
| 2,533,731 A | 12/1950 | Gomberg |
| 2,630,803 A | 3/1953 | Baran |
| 2,690,529 A | 9/1954 | Lindblad |
| 2,730,099 A | 1/1956 | Sullivan |
| 2,839,060 A | 6/1958 | Ormo |
| 2,936,141 A | 5/1960 | Rapata |

(Continued)

FOREIGN PATENT DOCUMENTS

DE            893 296       12/1953

(Continued)

*Primary Examiner*—Matthew F Desanto
(74) *Attorney, Agent, or Firm*—Brinks Hofer Gilson & Lione (57) ABSTRACT

The invention relates to an apparatus for adjustment of the length of an infusion tubing including a housing with cylinder part having a center axis, the housing further including at least one turnable unit. The apparatus is reusable. The system also enables the user to locate the apparatus anywhere on his body he may find suitable with regard to physiology and with regard to clothing. It is thus possible to arrange the apparatus underneath one's sweater, in one's waistband, pocket or the like. The simple adjustment of the apparatus is particularly suitable for the handicapped, and likewise it saves time for hospital staff in connection with patients who use infusion units.

11 Claims, 3 Drawing Sheets

U.S. PATENT DOCUMENTS

| | | |
|---|---|---|
| 2,952,420 A | 9/1960 | Von Hoorn |
| 3,055,361 A | 9/1962 | Ballard |
| 3,074,541 A | 1/1963 | Roehr |
| 3,107,785 A | 10/1963 | Roehr |
| 3,154,080 A | 10/1964 | Rowan et al. |
| 3,317,166 A | 5/1967 | Janssen |
| 3,545,286 A | 12/1970 | Stenstrom |
| 3,610,240 A | 10/1971 | Harautuneian |
| 3,648,999 A | 3/1972 | Bauer |
| 3,783,996 A | 1/1974 | Gerard et al. |
| 3,814,097 A | 6/1974 | Ganderton et al. |
| 3,831,729 A | 8/1974 | Howard |
| 3,840,011 A | 10/1974 | Wright |
| 3,865,236 A | 2/1975 | Rycroft |
| 3,942,528 A | 3/1976 | Loeser |
| 3,986,508 A | 10/1976 | Barrington |
| 4,014,328 A | 3/1977 | Cluff et al. |
| 4,022,205 A | 5/1977 | Tenczar |
| 4,146,113 A | 3/1979 | Gavel |
| 4,150,798 A | 4/1979 | Aragon |
| 4,188,950 A | 2/1980 | Wardlaw |
| 4,201,406 A | 5/1980 | Dennehey et al. |
| 4,227,528 A | 10/1980 | Wardlaw |
| 4,267,836 A | 5/1981 | Whitney et al. |
| 4,306,705 A | 12/1981 | Svensson |
| 4,315,505 A | 2/1982 | Crandall et al. |
| 4,334,551 A | 6/1982 | Pfister |
| D267,199 S | 12/1982 | Koenig |
| 4,365,630 A | 12/1982 | McFarlane |
| 4,400,861 A | 8/1983 | Parker |
| 4,406,042 A | 9/1983 | McPhee |
| 4,458,344 A | 7/1984 | Coogler |
| 4,472,024 A | 9/1984 | Konomura et al. |
| 4,473,369 A | 9/1984 | Lueders et al. |
| 4,500,312 A | 2/1985 | McFarlane |
| 4,517,971 A | 5/1985 | Sorbonned |
| 4,530,695 A | 7/1985 | Phillips et al. |
| 4,531,686 A | 7/1985 | Shaw |
| 4,576,846 A | 3/1986 | Noel |
| 4,606,735 A | 8/1986 | Wilder et al. |
| 4,610,469 A | 9/1986 | Wolff-Mooij |
| 4,616,790 A | 10/1986 | Beltran |
| 4,619,349 A | 10/1986 | Braun |
| 4,635,683 A | 1/1987 | Nielsen |
| 4,637,404 A | 1/1987 | Gessman |
| 4,662,873 A | 5/1987 | Lash et al. |
| 4,682,702 A | 7/1987 | Gach |
| 4,713,059 A | 12/1987 | Bickelhaupt et al. |
| 4,734,092 A | 3/1988 | Millerd |
| 4,755,173 A | 7/1988 | Konopka et al. |
| 4,758,020 A | 7/1988 | Boyd |
| 4,800,629 A | 1/1989 | Ikeda |
| 4,802,638 A | 2/1989 | Burger et al. |
| 4,817,603 A | 4/1989 | Turner et al. |
| RE32,922 E | 5/1989 | Levin et al. |
| 4,838,871 A | 6/1989 | Luther |
| 4,840,613 A | 6/1989 | Balbierz |
| 4,850,974 A | 7/1989 | Bickelhaupt et al. |
| 4,878,897 A | 11/1989 | Katzin |
| 4,895,570 A | 1/1990 | Larkin |
| D306,500 S | 3/1990 | Brahler |
| 4,913,369 A | 4/1990 | Lia et al. |
| 4,917,669 A | 4/1990 | Bonaldo |
| 4,935,010 A | 6/1990 | Cox et al. |
| 4,950,163 A | 8/1990 | Zimble |
| 4,950,252 A | 8/1990 | Luther et al. |
| 4,978,338 A | 12/1990 | Melsky et al. |
| 4,982,842 A | 1/1991 | Hollister |
| 4,986,817 A | 1/1991 | Code |
| 4,994,045 A | 2/1991 | Ranford |
| 5,011,475 A | 4/1991 | Olson |
| 5,024,662 A | 6/1991 | Menes et al. |
| 5,067,496 A | 11/1991 | Eisele |
| 5,077,872 A | 1/1992 | Guthammar |
| 5,083,757 A | 1/1992 | Barsky |
| 5,098,389 A | 3/1992 | Cappucci |
| 5,112,313 A | 5/1992 | Sallee |
| 5,116,319 A | 5/1992 | Van den Haak |
| 5,116,324 A | 5/1992 | Brierley et al. |
| 5,116,325 A | 5/1992 | Paterson |
| 5,121,751 A | 6/1992 | Panalletta |
| 5,134,593 A | 7/1992 | Logan et al. |
| 5,134,594 A | 7/1992 | Woo |
| 5,137,524 A | 8/1992 | Lynn et al. |
| 5,141,496 A | 8/1992 | Dalto et al. |
| 5,147,319 A | 9/1992 | Ishikawa et al. |
| 5,147,375 A | 9/1992 | Sullivan et al. |
| 5,161,681 A | 11/1992 | Kemp et al. |
| 5,163,915 A | 11/1992 | Holleron |
| 5,176,662 A | 1/1993 | Bartholomew et al. |
| 5,188,314 A | 2/1993 | Peters |
| 5,188,611 A | 2/1993 | Orgain |
| RE34,223 E | 4/1993 | Bonaldo |
| 5,222,947 A | 6/1993 | D'Amico |
| 5,232,454 A | 8/1993 | Hollister |
| 5,236,143 A | 8/1993 | Dragon |
| 5,240,199 A | 8/1993 | Peters |
| 5,248,301 A | 9/1993 | Koenig et al. |
| 5,256,152 A | 10/1993 | Marks |
| 5,257,980 A | 11/1993 | Van Antwerp et al. |
| 5,265,822 A | 11/1993 | Shober, Jr. et al. |
| 5,269,799 A | 12/1993 | Daniel |
| 5,279,579 A | 1/1994 | D'Amico |
| 5,279,591 A | 1/1994 | Simon |
| 5,282,793 A | 2/1994 | Larson |
| 5,300,030 A | 4/1994 | Crossman et al. |
| 5,312,359 A | 5/1994 | Wallace |
| 5,312,369 A | 5/1994 | Arcusin et al. |
| 5,316,246 A | 5/1994 | Scott et al. |
| 5,324,302 A | 6/1994 | Crouse |
| 5,342,319 A | 8/1994 | Watson et al. |
| 5,342,324 A | 8/1994 | Tucker |
| 5,343,637 A | 9/1994 | Schindler |
| 5,350,392 A | 9/1994 | Purcell et al. |
| 5,354,280 A | 10/1994 | Haber et al. |
| 5,366,469 A | 11/1994 | Steg et al. |
| 5,372,592 A | 12/1994 | Gambale |
| 5,376,082 A | 12/1994 | Phelps |
| 5,380,067 A | 1/1995 | Turvill et al. |
| 5,384,174 A | 1/1995 | Ward et al. |
| 5,387,197 A | 2/1995 | Smith et al. |
| 5,388,931 A | 2/1995 | Carlson |
| 5,390,669 A | 2/1995 | Stuart et al. |
| 5,391,151 A | 2/1995 | Wilmot |
| 5,403,288 A | 4/1995 | Stanners |
| 5,405,332 A | 4/1995 | Opalek |
| 5,429,607 A | 7/1995 | McPhee |
| 5,429,613 A | 7/1995 | D'Amico |
| 5,433,307 A | 7/1995 | Jeppe |
| D362,718 S | 9/1995 | Deily et al. |
| 5,449,349 A | 9/1995 | Sallee et al. |
| 5,487,506 A | 1/1996 | Drummond et al. |
| 5,490,841 A | 2/1996 | Landis |
| 5,492,313 A | 2/1996 | Pan et al. |
| 5,505,709 A | 4/1996 | Funderburk et al. |
| 5,507,730 A | 4/1996 | Haber et al. |
| 5,519,167 A | 5/1996 | Kunimoto et al. |
| 5,520,654 A | 5/1996 | Wahlberg |
| 5,522,803 A | 6/1996 | Teisson-Simony |
| 5,533,974 A | 7/1996 | Gaba |
| 5,540,709 A | 7/1996 | Ramel |
| 5,545,143 A | 8/1996 | Fischell |

| | | | | | | |
|---|---|---|---|---|---|---|
| 5,545,152 | A | 8/1996 | Funderburk et al. | 6,293,925 B1 | 9/2001 | Safabash et al. |
| 5,554,130 | A | 9/1996 | McDonald et al. | 6,302,866 B1 | 10/2001 | Marggi |
| 5,558,650 | A | 9/1996 | McPhee | 6,319,232 B1 | 11/2001 | Kashmer |
| 5,562,636 | A | 10/1996 | Utterberg | 6,322,535 B1 | 11/2001 | Hitchins et al. |
| 5,584,813 | A | 12/1996 | Livingston et al. | 6,322,808 B1 | 11/2001 | Trautman et al. |
| 5,591,188 | A | 1/1997 | Waisman | 6,334,856 B1 | 1/2002 | Allen et al. |
| 5,599,309 | A | 2/1997 | Marshall et al. | 6,355,021 B1 | 3/2002 | Nielsen et al. |
| 5,599,315 | A | 2/1997 | McPhee | 6,379,335 B1 | 4/2002 | Rigon et al. |
| 5,599,318 | A | 2/1997 | Sweeney et al. | D456,692 S | 5/2002 | Epstein |
| 5,628,765 | A | 5/1997 | Morita | 6,387,076 B1 | 5/2002 | Van Landuyt |
| 5,643,214 | A | 7/1997 | Marshall et al. | 6,488,663 B1 | 12/2002 | Steg |
| 5,643,216 | A | 7/1997 | White | 6,517,517 B1 | 2/2003 | Farrugia et al. |
| 5,643,220 | A | 7/1997 | Cosme | 6,520,938 B1 | 2/2003 | Funderburk et al. |
| 5,662,617 | A | 9/1997 | Odell et al. | D472,316 S | 3/2003 | Douglas et al. |
| 5,665,071 | A | 9/1997 | Wyrick | D472,630 S | 4/2003 | Douglas et al. |
| 5,665,075 | A | 9/1997 | Gyure et al. | 6,572,586 B1 | 6/2003 | Wojcik |
| 5,681,323 | A | 10/1997 | Arick | 6,579,267 B2 | 6/2003 | Lynch et al. |
| 5,695,476 | A | 12/1997 | Harris | 6,582,397 B2 | 6/2003 | Alesi et al. |
| 5,704,920 | A | 1/1998 | Gyure | 6,595,962 B1 | 7/2003 | Perthu |
| 5,709,516 | A | 1/1998 | Peterson et al. | 6,607,509 B2 | 8/2003 | Bobroff et al. |
| 5,714,225 | A | 2/1998 | Hansen et al. | 6,607,511 B2 | 8/2003 | Halseth et al. |
| 5,741,288 | A | 4/1998 | Rife | 6,629,949 B1 | 10/2003 | Douglas |
| 5,752,923 | A | 5/1998 | Terwilliger | 6,645,182 B1 | 11/2003 | Szabo |
| 5,810,835 | A | 9/1998 | Ryan et al. | 6,685,674 B2 | 2/2004 | Douglas et al. |
| 5,820,598 | A | 10/1998 | Gazza et al. | 6,702,779 B2 | 3/2004 | Connelly et al. |
| D402,538 | S | 12/1998 | Wagter et al. | 6,726,649 B2 | 4/2004 | Swenson et al. |
| 5,843,001 | A | 12/1998 | Goldenberg | 6,736,797 B1 | 5/2004 | Larsen et al. |
| 5,851,197 | A | 12/1998 | Marano et al. | 6,749,589 B1 | 6/2004 | Douglas et al. |
| 5,858,001 | A | 1/1999 | Tsals et al. | 6,790,199 B1 | 9/2004 | Gianakos |
| 5,865,806 | A | 2/1999 | Howell | 6,805,686 B1 | 10/2004 | Fathallah et al. |
| 5,873,540 | A | 2/1999 | Hardin | 6,811,545 B2 | 11/2004 | Vaillancourt |
| 5,899,886 | A | 5/1999 | Cosme | 6,814,720 B2 | 11/2004 | Olsen et al. |
| 5,913,846 | A | 6/1999 | Szabo | 6,824,530 B2 | 11/2004 | Wagner et al. |
| 5,915,640 | A | 6/1999 | Wagter et al. | 6,824,531 B1 | 11/2004 | Zecha, Jr. et al. |
| 5,919,167 | A | 7/1999 | Mulhauser et al. | 6,830,562 B2 | 12/2004 | Mogensen et al. |
| 5,925,032 | A | 7/1999 | Clements | 6,837,877 B2 | 1/2005 | Zurcher |
| 5,947,935 | A | 9/1999 | Rhinehart et al. | 6,840,922 B2 | 1/2005 | Nielsen et al. |
| 5,951,523 | A | 9/1999 | Osterlind et al. | 6,880,701 B2 | 4/2005 | Bergeron et al. |
| 5,954,643 | A | 9/1999 | VanAntwerp et al. | 6,916,017 B2 | 7/2005 | Noe |
| 5,957,892 | A | 9/1999 | Thorne | 6,923,791 B2 | 8/2005 | Douglas |
| 5,968,011 | A | 10/1999 | Larsen et al. | 6,926,694 B2 | 8/2005 | Marano-Ford et al. |
| 5,975,120 | A | 11/1999 | Novosel | 6,939,331 B2 | 9/2005 | Ohshima |
| 5,980,488 | A | 11/1999 | Thorne | 6,949,084 B2 | 9/2005 | Marggi et al. |
| 5,980,506 | A | 11/1999 | Mathiasen | 7,104,491 B2 * | 9/2006 | Vinding .................. 242/378.4 |
| 5,984,224 | A | 11/1999 | Yang | 2001/0004970 A1 | 6/2001 | Hollister et al. |
| 5,984,897 | A | 11/1999 | Petersen et al. | 2001/0016714 A1 | 8/2001 | Bell et al. |
| 5,992,787 | A | 11/1999 | Burke | 2001/0021827 A1 | 9/2001 | Ferguson et al. |
| D417,733 | S | 12/1999 | Howell et al. | 2001/0039401 A1 | 11/2001 | Ferguson et al. |
| 6,017,328 | A | 1/2000 | Fischell et al. | 2001/0041875 A1 | 11/2001 | Higuchi et al. |
| D421,119 | S | 2/2000 | Musgrave et al. | 2002/0022855 A1 | 2/2002 | Bobroff et al. |
| 6,019,304 | A * | 2/2000 | Skowronski et al. ........ 242/373 | 2002/0068904 A1 | 6/2002 | Pluth et al. |
| 6,039,629 | A | 3/2000 | Mitchell | 2002/0072720 A1 | 6/2002 | Hague et al. |
| 6,042,570 | A | 3/2000 | Bell et al. | 2002/0077599 A1 | 6/2002 | Wojcik |
| 6,045,533 | A | 4/2000 | Kriesel et al. | 2002/0107489 A1 | 8/2002 | Lee |
| 6,050,976 | A | 4/2000 | Thorne et al. | 2002/0111581 A1 | 8/2002 | Sasso |
| 6,056,718 | A | 5/2000 | Funderburk et al. | 2002/0145073 A1 | 10/2002 | Swanson |
| 6,065,708 | A * | 5/2000 | Matsubara ............... 242/388.1 | 2002/0156424 A1 | 10/2002 | Suzuki et al. |
| 6,074,371 | A | 6/2000 | Fischell | 2002/0156427 A1 | 10/2002 | Suzuki et al. |
| 6,086,008 | A | 7/2000 | Gray et al. | 2002/0161332 A1 | 10/2002 | Ramey |
| 6,086,575 | A | 7/2000 | Mejslov | 2002/0169419 A1 | 11/2002 | Steg |
| 6,090,068 | A | 7/2000 | Chanut | 2002/0173748 A1 | 11/2002 | McConnell et al. |
| 6,093,172 | A | 7/2000 | Funderburk et al. | 2002/0183688 A1 | 12/2002 | Lastovich et al. |
| 6,093,179 | A | 7/2000 | O'Hara et al. | 2002/0189688 A1 | 12/2002 | Roorda |
| 6,099,503 | A | 8/2000 | Stardella | 2002/0193737 A1 | 12/2002 | Popovsky |
| 6,105,218 | A | 8/2000 | Reekie | 2002/0193744 A1 | 12/2002 | Alesi et al. |
| 6,120,482 | A | 9/2000 | Szabo | 2003/0069548 A1 | 4/2003 | Connelly et al. |
| 6,123,690 | A | 9/2000 | Mejslov | 2003/0105430 A1 | 6/2003 | Lavi et al. |
| 6,132,755 | A | 10/2000 | Eicher et al. | 2003/0109829 A1 | 6/2003 | Mogensen et al. |
| 6,183,464 | B1 | 2/2001 | Sharp et al. | 2003/0125669 A1 | 7/2003 | Safabash et al. |
| 6,193,694 | B1 | 2/2001 | Bell et al. | 2003/0125678 A1 | 7/2003 | Swenson et al. |
| 6,219,574 | B1 | 4/2001 | Cormier et al. | 2003/0130619 A1 | 7/2003 | Safabash et al. |
| 6,221,058 | B1 | 4/2001 | Kao et al. | 2003/0139704 A1 | 7/2003 | Lin |
| 6,248,093 | B1 | 6/2001 | Moberg | 2003/0158520 A1 | 8/2003 | Safabash et al. |

| Pub. No. | Date | Inventor |
|---|---|---|
| 2003/0176843 A1 | 9/2003 | Wilkinson |
| 2003/0181863 A1 | 9/2003 | Davis et al. |
| 2003/0181868 A1 | 9/2003 | Swenson |
| 2003/0181873 A1 | 9/2003 | Swenson |
| 2003/0181874 A1 | 9/2003 | Bressler et al. |
| 2003/0187394 A1 | 10/2003 | Wilkinson et al. |
| 2003/0187395 A1 | 10/2003 | Gabel et al. |
| 2003/0199823 A1 | 10/2003 | Bobroff et al. |
| 2003/0216686 A1 | 11/2003 | Lynch et al. |
| 2003/0225373 A1 | 12/2003 | Bobroff et al. |
| 2003/0225374 A1 | 12/2003 | Mathiasen |
| 2003/0229308 A1 | 12/2003 | Tsals et al. |
| 2003/0229316 A1 | 12/2003 | Hwang et al. |
| 2004/0002682 A1 | 1/2004 | Kovelman et al. |
| 2004/0006316 A1 | 1/2004 | Patton |
| 2004/0026840 A1 | 2/2004 | Eckel et al. |
| 2004/0044306 A1 | 3/2004 | Lynch et al. |
| 2004/0049159 A1 | 3/2004 | Barrus et al. |
| 2004/0068231 A1 | 4/2004 | Blondeau |
| 2004/0087913 A1 | 5/2004 | Rogers et al. |
| 2004/0111068 A1 | 6/2004 | Swenson |
| 2004/0112781 A1 | 6/2004 | Hofverberg et al. |
| 2004/0116865 A1 | 6/2004 | Bengtsson |
| 2004/0138612 A1 | 7/2004 | Shermer et al. |
| 2004/0138620 A1 | 7/2004 | Douglas et al. |
| 2004/0143216 A1 | 7/2004 | Douglas et al. |
| 2004/0143218 A1 | 7/2004 | Das |
| 2004/0158202 A1 | 8/2004 | Jensen |
| 2004/0158207 A1 | 8/2004 | Hunn et al. |
| 2004/0162518 A1 | 8/2004 | Connelly et al. |
| 2004/0171989 A1 | 9/2004 | Horner et al. |
| 2004/0178098 A1 | 9/2004 | Swenson et al. |
| 2004/0186446 A1 | 9/2004 | Ohshima |
| 2004/0199123 A1 | 10/2004 | Nielsen |
| 2004/0204687 A1 | 10/2004 | Mogensen et al. |
| 2004/0204690 A1 | 10/2004 | Yashiro et al. |
| 2004/0220528 A1 | 11/2004 | Garcia, Jr. |
| 2004/0238392 A1 | 12/2004 | Peterson et al. |
| 2004/0243065 A1 | 12/2004 | McConnell et al. |
| 2004/0254433 A1 | 12/2004 | Bandis et al. |
| 2004/0260235 A1 | 12/2004 | Douglas |
| 2004/0260250 A1 | 12/2004 | Harris et al. |
| 2005/0035014 A1 | 2/2005 | Cane |
| 2005/0101932 A1 | 5/2005 | Cote et al. |
| 2005/0101933 A1 | 5/2005 | Marrs et al. |
| 2005/0107743 A1 | 5/2005 | Fangrow, Jr. |
| 2005/0113761 A1 | 5/2005 | Faust et al. |
| 2005/0119637 A1 | 6/2005 | Lundgren et al. |
| 2005/0124936 A1 | 6/2005 | Mogensen et al. |
| 2005/0159709 A1 | 7/2005 | Wilkinson |
| 2005/0215979 A1 | 9/2005 | Kornerup et al. |
| 2005/0251098 A1 | 11/2005 | Wyss et al. |
| 2005/0277892 A1 | 12/2005 | Chen |
| 2005/0283114 A1 | 12/2005 | Bresina et al. |
| 2006/0030815 A1 | 2/2006 | Csincsura et al. |

FOREIGN PATENT DOCUMENTS

| | | |
|---|---|---|
| DE | 1 053 541 | 3/1959 |
| DE | 26 20 009 A1 | 12/1977 |
| DE | 28 03 509 | 8/1979 |
| DE | 28 03 509 A | 8/1979 |
| DE | 37 15 965 A | 1/1988 |
| DE | 37 22 893 C1 | 6/1988 |
| DE | 38 23 447 | 2/1996 |
| DE | 196 31 921 | 3/1997 |
| DE | 196 10 692 A1 | 9/1997 |
| DE | 298 18 311 U1 | 3/1999 |
| DE | 298 18 311 U1 | 11/1999 |
| DE | 198 47 143 A1 | 1/2000 |
| DE | 19847143 A1 | 1/2000 |
| DE | 299 21 406 | 1/2001 |
| DE | 100 49 001 A1 | 4/2002 |
| DE | 101 06 074 A1 | 6/2002 |
| DE | 299 21 406 U1 | 11/2002 |
| EP | 0 188 014 B1 | 10/1985 |
| EP | 0 239 244 B1 | 2/1987 |
| EP | 0 298 521 B1 | 9/1990 |
| EP | 0 184 231 B1 | 1/1992 |
| EP | 0 475 857 | 3/1992 |
| EP | 0 544 837 B1 | 6/1993 |
| EP | 0 633 039 | 7/1994 |
| EP | 0 651 662 B1 | 5/1995 |
| EP | 0 714 631 B1 | 6/1996 |
| EP | 744 183 A2 | 11/1996 |
| EP | 0 747 006 A1 | 12/1996 |
| EP | 0 688 232 B1 | 12/1998 |
| EP | 0 884 108 A1 | 12/1998 |
| EP | 0 916 361 A1 | 5/1999 |
| EP | 0 931 560 A1 | 7/1999 |
| EP | 0 956 879 A1 | 11/1999 |
| EP | 1 045 145 A1 | 10/2000 |
| EP | 1 060 757 A1 | 12/2000 |
| EP | 1 086 718 A | 3/2001 |
| EP | 1 125 593 A1 | 8/2001 |
| EP | 1 167 765 A2 | 1/2002 |
| EP | 0 775 501 | 6/2002 |
| EP | 0 894 216 B1 | 7/2003 |
| EP | 1 380 315 A1 | 1/2004 |
| FR | 576 849 | 8/1924 |
| FR | 576849 | 8/1924 |
| FR | 2 611 013 | 8/1988 |
| FR | 2725902 | 10/1994 |
| FR | 2 733 915 | 11/1996 |
| FR | 2733915 A1 | 11/1996 |
| FR | 2 781 617 A1 | 1/2000 |
| FR | 2781617 A1 | 1/2000 |
| GB | 478803 | 1/1938 |
| GB | 591730 | 3/1946 |
| GB | 906574 | 9/1962 |
| GB | 1 268 575 | 3/1972 |
| GB | 1 403 034 | 8/1975 |
| GB | 2 224 808 A | 5/1990 |
| GB | 2 270 552 A | 3/1994 |
| JP | 5326062 A | 12/1993 |
| JP | 05326062 A | 12/1993 |
| JP | 7051251 | 11/1995 |
| JP | 9217584 A | 9/1997 |
| JP | 2000-59877 A | 2/2000 |
| JP | 3140740 | 2/2000 |
| JP | 2000059877 A | 2/2000 |
| JP | 3140740 B2 | 3/2001 |
| JP | 2002-028246 | 1/2002 |
| NL | 1017427 C | 11/2002 |
| WO | WO 87/06474 | 11/1987 |
| WO | WO 93/03787 | 3/1993 |
| WO | WO 93/05840 | 4/1993 |
| WO | WO 94/20160 | 9/1994 |
| WO | WO 95/28327 A | 10/1995 |
| WO | WO 96/35472 A1 | 11/1996 |
| WO | WO 98/09065 | 3/1998 |
| WO | WO 98/58693 | 12/1998 |
| WO | WO 99/07435 | 2/1999 |
| WO | WO 99/33504 | 7/1999 |
| WO | WO 99/36009 | 7/1999 |
| WO | WO 99/56802 | 11/1999 |
| WO | WO 99/61815 | 12/1999 |
| WO | WO 00/02614 | 1/2000 |
| WO | WO 00/03757 | 1/2000 |
| WO | WO 00/44324 A1 | 8/2000 |
| WO | WO 01/04507 A1 | 1/2001 |
| WO | WO 01/30419 A2 | 5/2001 |
| WO | WO 01/68180 | 9/2001 |
| WO | WO 01/81785 A1 | 11/2001 |
| WO | WO 01/93926 A2 | 12/2001 |
| WO | WO 02/068014 | 1/2002 |

| WO | WO 02/46080 | 6/2002 |
| WO | WO 02/066854 A1 | 8/2002 |
| WO | WO 02/094352 | 11/2002 |
| WO | WO 02/100457 | 12/2002 |
| WO | WO 03/015860 A1 | 2/2003 |
| WO | WO 03/026728 | 4/2003 |
| WO | WO 2004/030726 A | 4/2004 |
| WO | WO 2004/087240 | 10/2004 |
| WO | WO 2005/004973 | 1/2005 |

* cited by examiner

APPARATUS AND METHOD FOR ADJUSTMENT OF THE LENGTH OF AN INFUSION TUBING

This application is a continuation of International Application No. PCT/DK2003/000572, filed Sep. 2, 2003, which is a continuation of Danish Application No. PA 2002 01286, filed Sep. 2, 2002, these references are incorporated herein in their entirety.

FIELD OF THE INVENTION

The invention relates to an apparatus for adjustment of the length of an infusion tubing, comprising a housing with cylinder part including a central axis, said housing further comprising at least one turnable unit.

The invention also relates to a method for adjustment of the length of an infusion tubing by means of an apparatus comprising a housing with cylinder part including a central axis, said housing further comprising at least one turnable unit.

BACKGROUND

When infusion kits are used in combination with an insulin pump it is necessary to use a tubular element of a certain length, since the distance between the insulin pump and the cannula housing will vary. This variation in the distance between pump and cannula occurs ia during the night when the pump sits on the nightstand. In that case the tubing may be used in its full length. When, during the daytime, the pump is arranged in the belt of the diabetic, the requisite tubing length will be shorter—but still variable, since the cannula may be inserted in different places in the body.

Therefore the problem of excessive tubing may occur that the user may find difficult to arrange/conceal. That means that when cannula housing is arranged in the immediate vicinity of the pump and the user simultaneously uses a long tubing of 110 cm, a worst case scenario will involve about 90 cm that are not "in use".

It is desired to develop a winding device that is able to compensate for the above-described problem.

The winding device is typically located close to the skin— underneath the clothes. Optionally by means of a clip to the trouser waistband.

The winding device must not be able to cause failures of any kind in the supply of insulin; neither by damage to/deformation of tubing nor in any other way.

WO 96/35472 teaches an apparatus of the kind described above; it describes a portable medical pump wherein a winding unit is integrated for the infusion tubing. The drawback of this system is that, apart from the tubing constituting an integral part of the pump device, such system is mechanically complex and restricts the place where the winding may occur to a place near the infusion part and not anywhere on the tubing nor on just any tubing, the winding system being designed exclusively for the pump of which it is an integral part. To the user the system is not particularly flexible, since it is not possible to locate the pump unit and the winding unit apart. Therefore the unit will be very visible to the user when he wears the pump unit.

BRIEF SUMMARY OF THE INVENTION

It is thus the object of the present invention to provide an apparatus wherein the above-referenced drawbacks are overcome, and whereby it is possible to perform a winding of an infusion tubing to adjust the connecting length between pump and the infusion site, the apparatus being independent of infusion cannula and pump. Thus the apparatus enables reuse due to said independence. The system also makes it possible for the user to locate the winding unit anywhere on the body he finds suitable with regard to physiology and with regard to clothing. It is thus an option to arrange it underneath one's sweater, in one's waistband, pocket or the like.

Moreover, an automatic winder is obtained and wherein length increases and reductions are accomplished in a simple manner. The structure is also suitable for the handicapped and, likewise, it is a time-saving device for use by hospital staff in the context of patients who use infusion units, the unit being able to accommodate a considerably long tubing, and wherein the staff is thus able to adjust the length of the tubing in a simple manner, depending on whether the patient is confined to his bed and needs a relatively long tubing from and infusion pump to the patient in his bed, or whether the patient is not confined to his bed and has an infusion device/ pump arranged on his body, which means that the tubular connection between that and the site of infusion needs to be short.

This object is accomplished by means of an apparatus of the kind described above and wherein the housing also comprises a first axle, the centre axis of which coincides with the centre axis of the axle, and about which axle the turnable unit turns.

The object is also accomplished by a method of the kind described above, and wherein a first length of tubing is wound around the axle; a second length of tubing is wound around parts of the turnable unit; and a first free end portion and a second free end portion are situated outside the housing.

The apparatus works in that a tubing is mounted in the housing such that, from the housing, two free tubular elements extend, where the one tubular element is connected to an infusion cannula, and wherein the second tubular element is connected to an infusion pump. The two tubing ends will typically be configured such that the one tubing end is adjustable in length, while the second tubing end has a fixed distance to the housing as such. About half of the tubing is wound around a so-called cylinder part situated within the housing proper and being fixedly/non-turnably journalled, albeit it may also be turnable. The tubing is conveyed around an auxiliary means within the housing as such, designated a return wheel, such that the tubing is caused to proceed to an upper rotatable wheel, and wherein the tubing is, in relation to the cylinder part, extending in the one direction of rotation, while the tubing wound around the rotatable winder wheel will be extending in the opposite direction. The free end of the tubing is subsequently led out through the housing. The tubing length is distributed such that there are equal lengths of tubing wound on the cylinder part and the rotating winder wheel, respectively.

When a pull is thus exerted at the end of the tubing that is in direct communication with the rotating winder wheel, the following occurs:

The tubing is unwound from the rotating wheel and thus constitutes the extension. The rotating wheel turns on the axle due to the pull that is exerted on the tubing, and due to the internal construction tubing will be conveyed from the lower cylinder part to the rotating wheel. The construction of the individual elements means that the transfer from the one wheel to the other will constitute a length of tubing, whose length is half that unwound from the cylinder part.

Finally, it is an option to let a part of the interior, corresponding to the part designated the partition plate, be spring-biased such that it is possible to have the tubing pulled into the apparatus.

According to one aspect of the invention including a cylinder part and a wheel part that are rotatable relative to each other, one end of the tubing can be pulled out of the housing. The term 'stationary' as used in this context is intended to designate 'non-turnable' and 'immovable'.

According to another aspect of the invention including a cylinder part that is a stationary axle, both ends of the tubing can be pulled out of the housing.

According to another aspect of the invention the apparatus may include a cylinder part that is a turnable axle, a return wheel that is turnable about a first axle mounted on a partition plate. An aspect of the invention may also include a spring connected to the partition plate and to a part which is stationary in the housing.

By providing an apparatus according to another aspect of the invention where the diameter of the cylinder part and the wheel part are essentially identical, it is an option to automatically pull the tubing back into the housing again.

By providing an apparatus according to another aspect of the invention convenient exchange is accomplished between the two cylinder parts.

The invention also relates to a method for adjusting the length of an infusion tubing.

BRIEF DESCRIPTION OF THE DRAWINGS

The invention will now be explained in further detail with reference to the drawing, wherein.

DETAILED DESCRIPTION OF THE INVENTION

Figure 1:
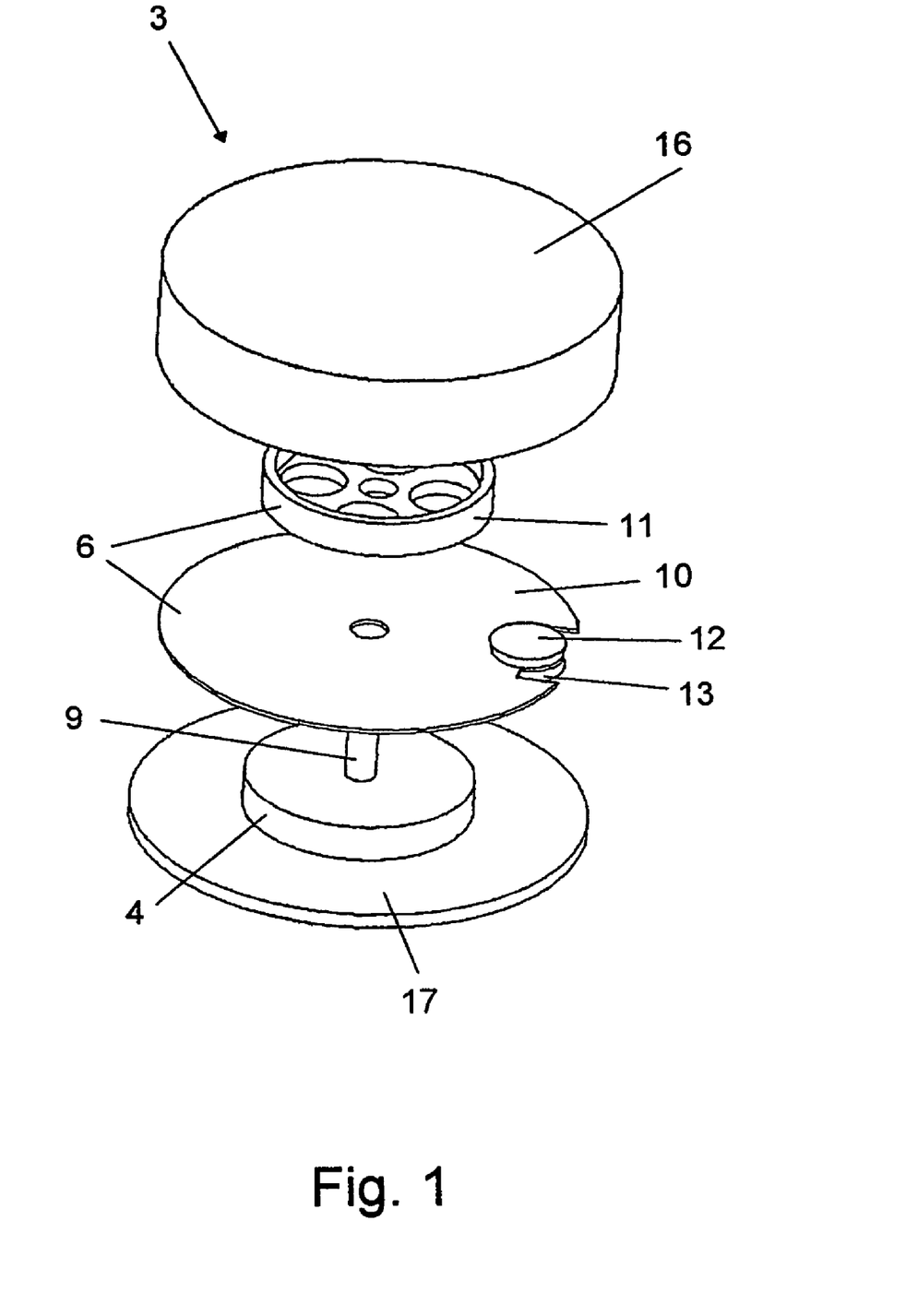
FIG. 1 is an exploded view of an apparatus according to the invention containing the individual elements.

FIG. 1 shows an apparatus 1 in an exploded view, with a housing 3 and comprising an upper part 16 and a lower part 17. Both the upper and the lower parts are circularly configured pieces, wherein the lower part is plate-shaped. Coaxially on this plate, cylinder part 4 is arranged, in this case also designated fixed winder wheel/stationary axle, about which a part of an infusion tubing 2 can be wound. It is noted that the cylinder part 4 can be turnable and/or it can be locked by means of e.g. a manually operated lock. In this embodiment, the cylinder part 4, however, is not turnable. In parallel with the axis and coincident therewith, a first axle 9 extends, and on said first axle 9 a first plate 10, also designate the partition plate, is arranged. Thus, the partition plate 10 has a through-going bore, through which the axle 9 extends. In the periphery of the partition plate 10, a rectangular slit is provided, in which a circular plate is secured, also designated return wheel 12, the diameter of which is considerably less than the diameter of the partition plate and about one third thereof, and wherein the outer periphery of said return wheel is flush with the periphery of the partition plate or is located within same.

Laterally to said return wheels, recesses 13 are shown that are configured to be so wide that the tubing is able to travel therethrough. In parallel with the axis of said partition plate and above there is arranged a rotating winder wheel/turnable wheel 11 that also comprises a through-going central bore that encircles the first axle 9.

This winder wheel is rotatable and, besides, the partition plate is also turnable about the axle 9. The rotatable winder wheel and the partition plate 10 constitute the turnable unit 6.

The tubing is also wound around the rotating winder wheel, from which an end part extends. Finally the housing ends at the top in an upper part 16 configured as a partially cylindrical dish that encircles the turnable unit 6 and ends close to the lower part 17 of the housing.

Figure 2:
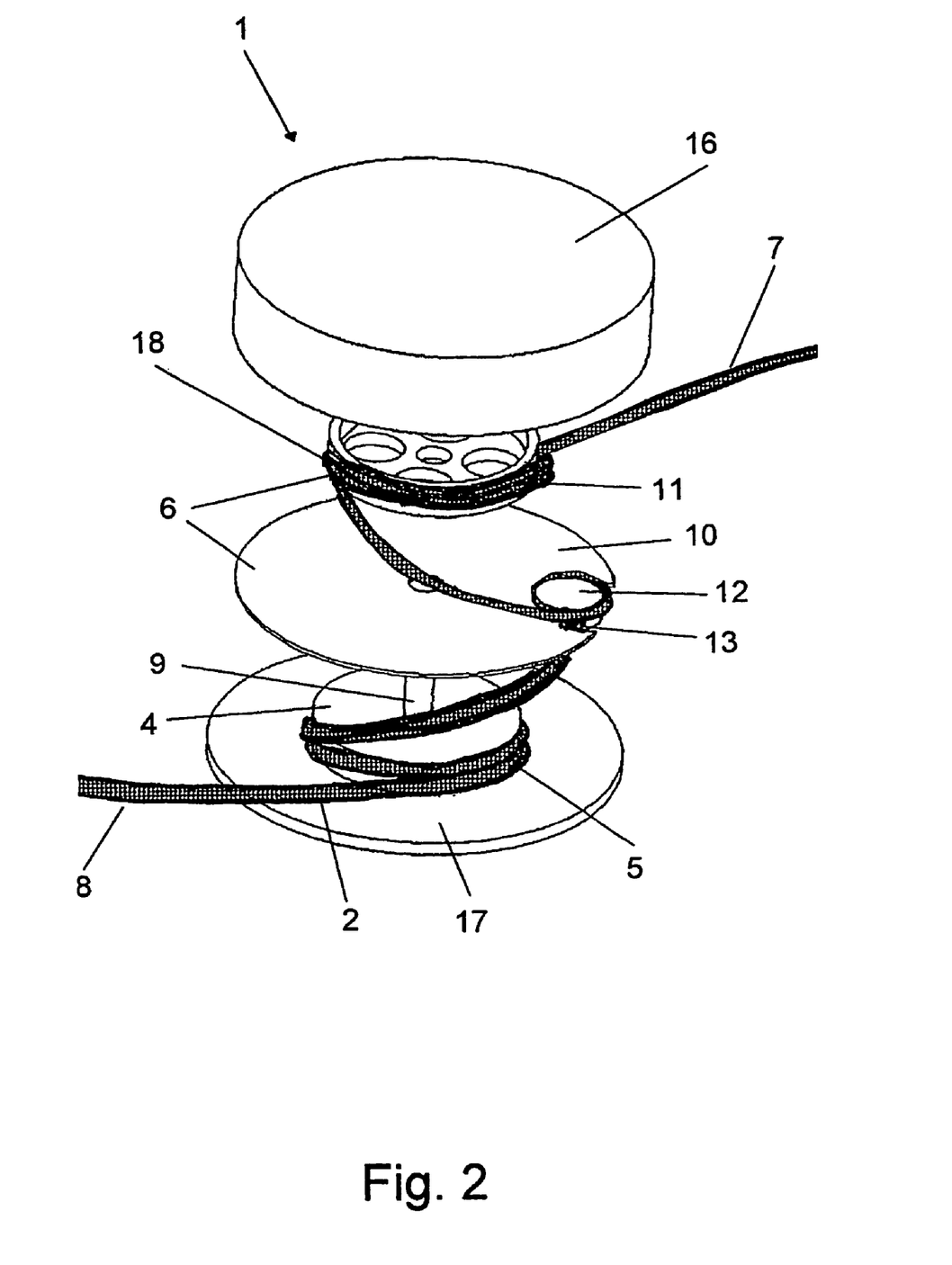
FIG. 2 shows the apparatus shown in FIG. 1, but wherein the location of the tubing in relation to the individual constituent components is indicated.

FIG. 2 is identical to FIG. 1, but the tubing 2 is shown herein in its mounted state. As will appear, the tubing 2 extends into the housing in one direction and is wound around the fixed winder wheel, eg counter-clockwise. From here the tubing proceeds up through the recess 13 and is wound around the return wheel, following which the tubing is conveyed around rotating winder wheel 11, where this winding extends opposite the winding of the fixed winder wheel, ie clockwise. From here the tubing exits.

The functioning of the apparatus 1 is that the tubing 2 is conveyed into the winder such that a short length of the tubing 2 allows coupling to e.g. a pump. About half of the tubing, designated the first length of tubing 5, is wound around the cylinder part 4. The tubing is subsequently conveyed around the return wheel 12. The return wheel is mounted on the plate 10 that separates the fixed and the rotating winder wheel. The return wheel ensures that the tubing is wound onto the rotating winder wheel 11 and the cylinder part 4 in each their direction, ie clockwise/counter-clockwise. Simultaneously the return wheel 12 conveys the tubing 2 past the partition plate 10, such that the tubing 2 is conveyed from the cylinder part 4 to the rotating winder wheel 11. The remainder of the tubing and designated the second length of tubing 18 is wound onto the rotating winder wheel 11. There are equal amounts of tubing wound on the two winder wheels in this example. When extension of the tubing is to be accomplished, the following occurs: the tubing 2 is unwound from the rotating wheel 11 by a pull in the length of tubing 7. The rotating wheel 11 turns about the axle 9, whereby the return wheel 12 will be forced to follow. Since, via the partition plate 10, the return wheel 12 rotates about the central axle 9, tubing will be transferred from the fixed to the rotating wheel.

Likewise, the return wheel 12 moves half the distance of the length of tubing unwound. This transfer will constitute a length of tubing, whose length is half that of the section that is unwound from the winder. Since the return wheel 12 is relieved the rotating winder wheel 11 by twice half of the length of the unwound length of tubing, the requisite length of tubing is accomplished that is required in order for the rotating winder wheel 11 to supply the user with the desired length of tubing.

Simultaneously the return wheel 12 has moved just as much in relation to the cylinder part 4 that has unwound precisely the length of tubing that was transferred to the rotating winder wheel.

The above explanation presupposes that the dimensions of the individual elements are adapted in relation to each other; in this example a diameter D being used for the fixed winder wheel and the rotating winder wheel, while the partition plate as such has a diameter which is twice that. However, other dimensions and hence other exchange ratios may apply.

It should also be mentioned that both the cylinder part and the rotating winder wheel have a height corresponding to the height of the winding of the tubing, and it follows that this height is a function of how much tubing is desired to be stored in the apparatus. The partition plate as such is relatively thin, its object being ia to carry the return wheel 12, which—as it is—is also rotatable about an axle mounted in the partition plate.

Thus, in its simplicity the winder consist of a minimum of seven parts, viz.

A housing that contains the winder mechanism and which is approximately cylinder-shaped;
A central axle secured along the central axle of the housing;
A cylinder part secured on the axle;
A partition plate mounted on the axle after the cylinder part;
A return wheel mounted on the partition plate; the axle of the return wheel being displaced in relation to the central axle such that the return wheel does not overlap the cylinder part or the rotating wheel;
A spring configured in such a manner that it seeks to rotate the partition plate in that direction, whereby the tubing is tightened;
A rotating winder wheel mounted on the central axle.

Thus FIG. 2 does not show the spring, but as mentioned it is located on the partition plate 10 and secured to the inner faces of the housing, whereby it is possible to tighten the tubing.

Figure 3:
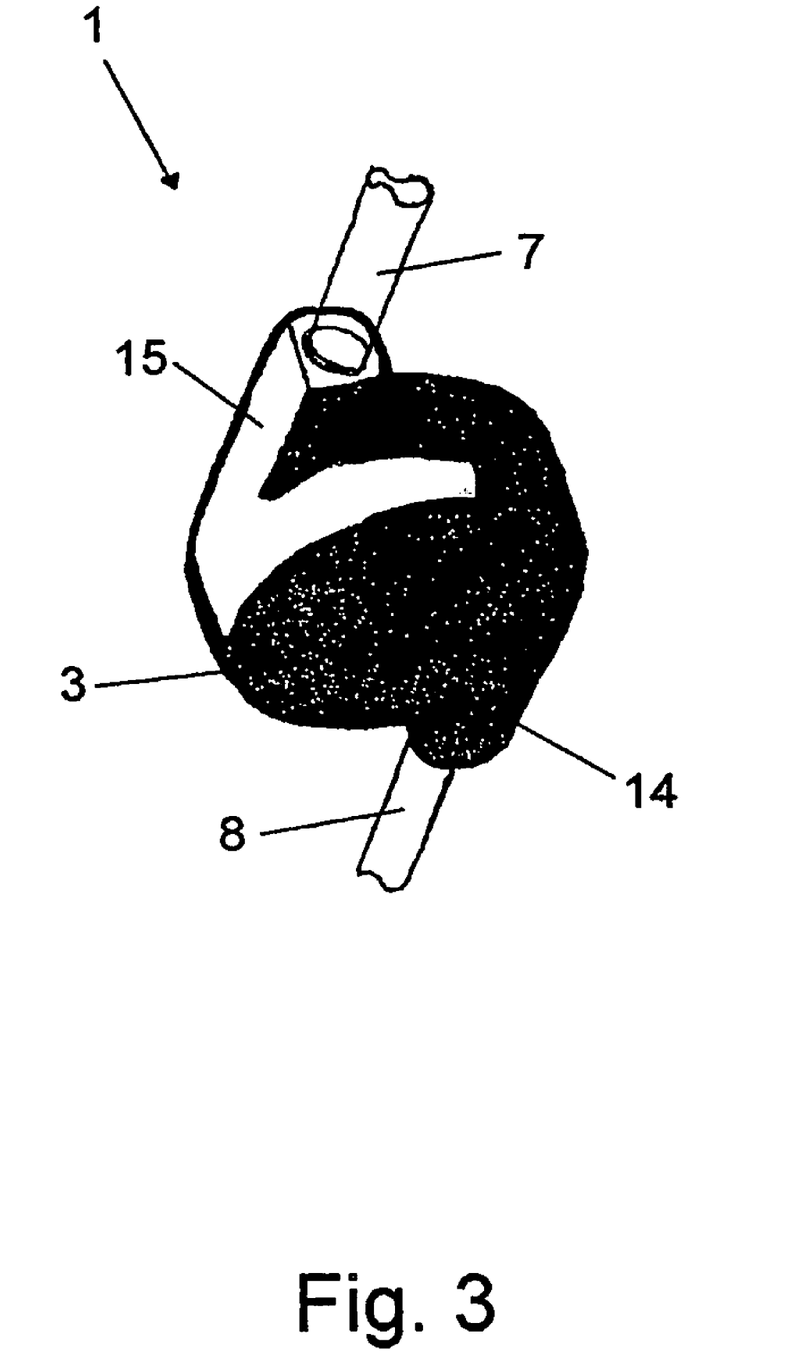
FIG. 3 shows an apparatus according to the invention, seen in a perspective view.

Finally FIG. 3 provides a perspective view of the apparatus, wherein it comprises a hosing 3 with a tubing 2, from where a first end part and a second end part 7, 8 will appear that protrude from the first and second tubing branches 14, 15, respectively. Expediently the two exits for the first end part and the second end part, respectively, are situated diametrically opposite each other. The one end part can be extended, while the second end part has a stationary distance to the housing, or conversely.

Besides, it should be noted that the apparatus can be configured such that both ends on the tubing can be pulled outwards. That is, the cylinder part 4 and the turnable wheel 11 can both be turnable. Both units can also be made non-turnable by means of a lock. In this manner the patient himself is able to regulate which of the two units is to be turnable and hence which of the tubing ends is to be adjustable in length, including optionally both ends.

The invention claimed is:

1. An apparatus for adjustment of the length of an infusion tubing, the apparatus comprising:
    a housing comprising:
        a cylinder part comprising a centre axis,
        a first axle arranged about the centre axis of the cylinder part, and
        at least one turnable unit turnable about the first axle, the at least one turnable unit comprising a partition plate turnable about the first axle and a wheel part turnable independently to the partition plate and about the same first axle, the partition plate comprising a return wheel, the return wheel being arranged at a periphery of the partition plate such that the return wheel rotates with the partition plate about the first axle, wherein the return wheel is configured to receive a portion of the length of tubing around a periphery of the return wheel.

2. An apparatus according to claim 1, wherein the apparatus comprises a spring, said spring being connected to the partition plate and to a part which is stationary within the housing.

3. An apparatus according to claim 2, wherein the spring is connected to the partition plate and to a wall of the housing.

4. An apparatus according to claim 1, wherein said cylinder part and wheel part are rotatable relative to each other.

5. An apparatus according to claim 1 wherein the cylinder part is a stationary axle.

6. An apparatus according to claim 1 wherein the cylinder part is a turnable axle.

7. An apparatus according to claim 1, wherein the return wheel is turnable about an axle mounted on the partition plate.

8. An apparatus according to claim 1, wherein a diameter of the cylinder part and a diameter of the turnable wheel part are essentially identical.

9. A method for adjustment of the length of an infusion tubing using an apparatus comprising a housing a cylinder part comprising a centre axis, a first axle arranged about the centre axis of the cylinder part, and at least one turnable unit turnable about the first axle, said turnable unit comprising a partition plate turnable about the first axle and a wheel part turnable independently to the partition plate about the same first axle, the partition plate comprising a return wheel positioned at a periphery of the partition plate so that the return wheel rotates with the partition plate about the first axle, the method comprising:
    winding a first length of tubing around the cylinder part;
    winding a second length of tubing around the wheel;
    positioning a first free end part and a second free end part of the tubing exteriorly of the housing,
    winding the first length of the tubing around said return wheel associated with the turnable unit and the turnable wheel part; and
    pulling the first end part, the second end part or both to adjust the length of the tubing extending exteriorly to the housing.

10. A method according to claim 9, comprising transferring the tubing situated around the cylinder part to the turnable unit and conversely during adjustment of the length of the tubing.

11. A method according to claim 9, comprising winding the first length of the tubing about the cylinder part in a first direction and winding the second length of the tubing around parts of the turnable unit in a second direction opposite the first direction.

* * * * *